(12) United States Patent
Shin et al.

(10) Patent No.: US 8,425,906 B2
(45) Date of Patent: Apr. 23, 2013

(54) METHOD TO INHIBIT CANCER TARGETING CD24

(75) Inventors: Young Kee Shin, Seoul (KR); Yoon-La Choi, Seoul (KR); Young Woo Park, Daejeon-si (KR); Seung Hyun Lee, Anyang-si (KR); Kyoung Song, Incheon (KR)

(73) Assignee: SNU R&DB Foundation, Seoul (KR)

( * ) Notice: Subject to any disclaimer, the term of this patent is extended or adjusted under 35 U.S.C. 154(b) by 98 days.

(21) Appl. No.: 12/307,108

(22) PCT Filed: Jul. 2, 2007

(86) PCT No.: PCT/KR2007/003202
§ 371 (c)(1),
(2), (4) Date: Dec. 30, 2008

(87) PCT Pub. No.: WO2008/002112
PCT Pub. Date: Jan. 3, 2008

(65) Prior Publication Data
US 2010/0166649 A1 Jul. 1, 2010

(30) Foreign Application Priority Data
Jun. 30, 2006 (KR) .................. 10-2006-0061119

(51) Int. Cl.
*A61K 39/395* (2006.01)
(52) U.S. Cl.
USPC ..................... 424/138.1; 424/139.1

(58) Field of Classification Search ................ None
See application file for complete search history.

(56) References Cited

U.S. PATENT DOCUMENTS
5,686,072 A 11/1997 Uhr et al.

OTHER PUBLICATIONS

Harlow, Antibodies A Laboratory Manual, 1998, pp. 72-76.*
Knight (BioTechnology vol. 7 No. 1, Jan. 1989).*
Chen et al., "Inhibition of Human CD24 Binding to Platelet-bound P-selectin by Monoclonal Antibody," *Proc. West. Pharmacol. Soc.*, 47:28-29, (2004).
International Search report for PCT Application No. PCT/KR2007/003202; 4 pp., (Oct. 5, 2007).
Smith et al., "The Metastasis-Associated Gene CD24 is Regulated by Ral GTPase and is a Mediator of Cell Proliferation and Survival in Human Cancer," Cancer Res., 66(4):1917-1922, (Feb. 15, 2006).
Written Opinion for PCT Application No. PCT/KR2007/003202, 5 pp. (Oct. 4, 2007).

* cited by examiner

*Primary Examiner* — Sheela J Huff
(74) *Attorney, Agent, or Firm* — The PL Law Group, PLLC

(57) ABSTRACT

The present invention relates to a method to inhibit cancer by targeting CD24, more precisely a method to inhibit cancer by using CD24 expressed in most cancer cells as a target of an antibody therapeutic agent or by inhibiting the interaction between CD24 and P-selectin. CD24 is over-expressed in most cancer cells and CD24 accumulated in cytoplasm accelerates metastasis. Therefore, the method to inhibit cancer of the invention by targeting CD24 can be effectively used for the treatment of cancer by inhibiting the progress of various cancers over-expressing CD24.

15 Claims, 13 Drawing Sheets

[Fig. 1]
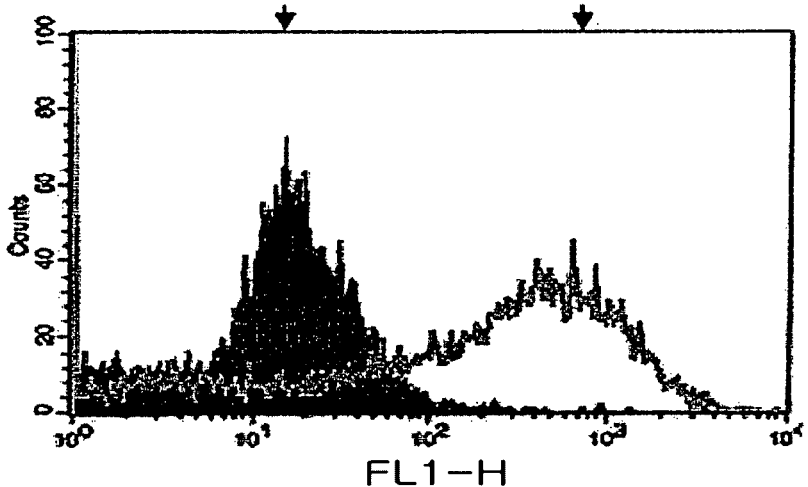
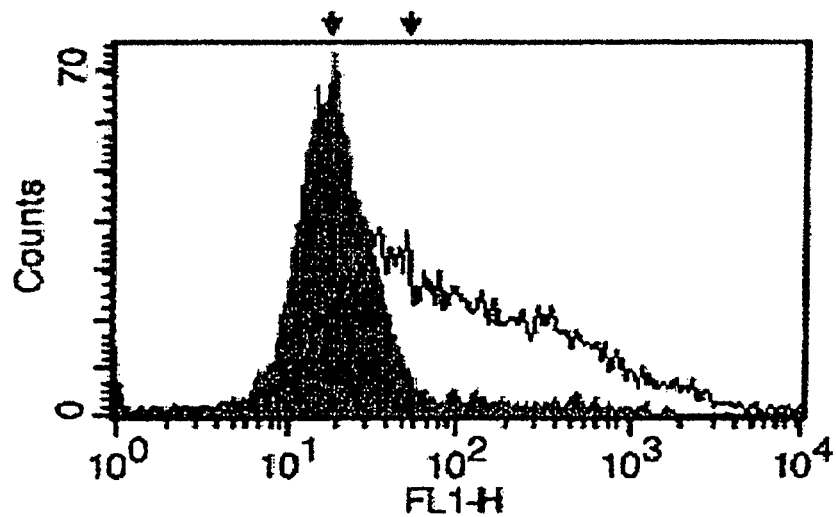

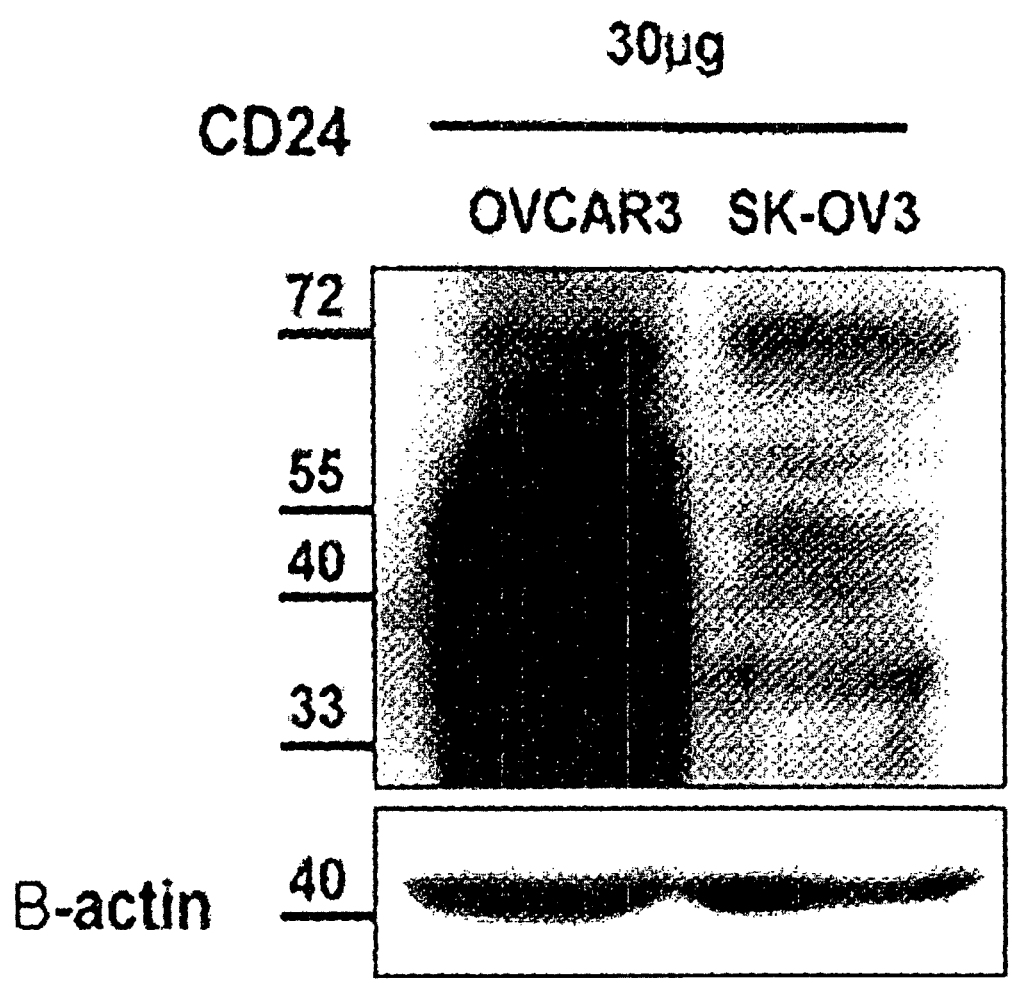

[Fig. 3]
SK-OV3

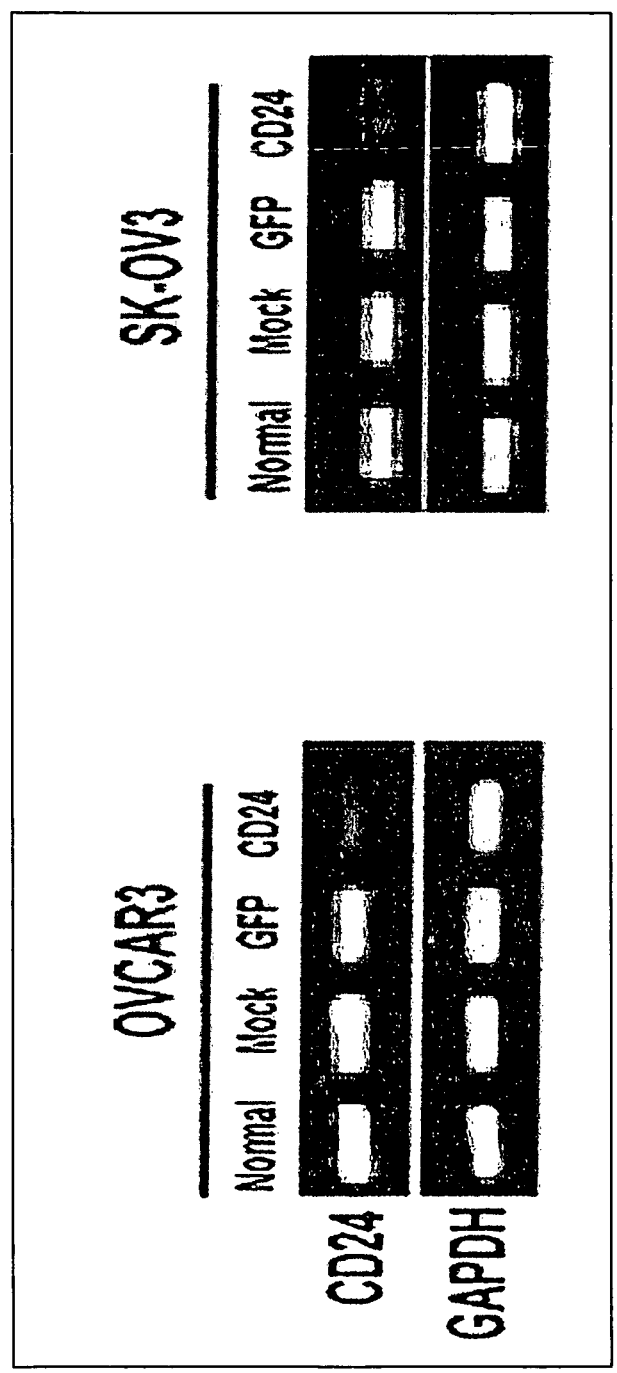
[Fig. 4]

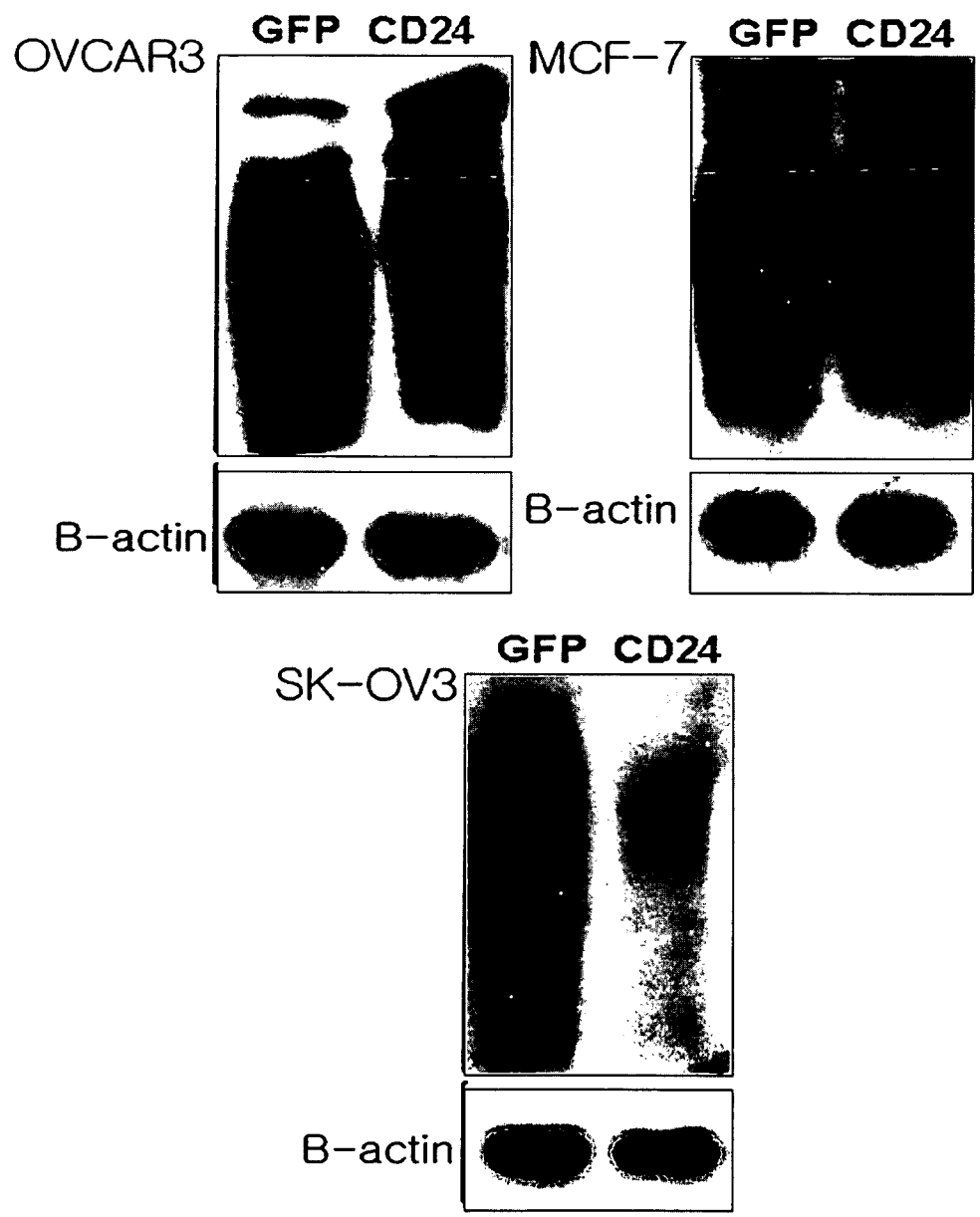
[Fig. 5]

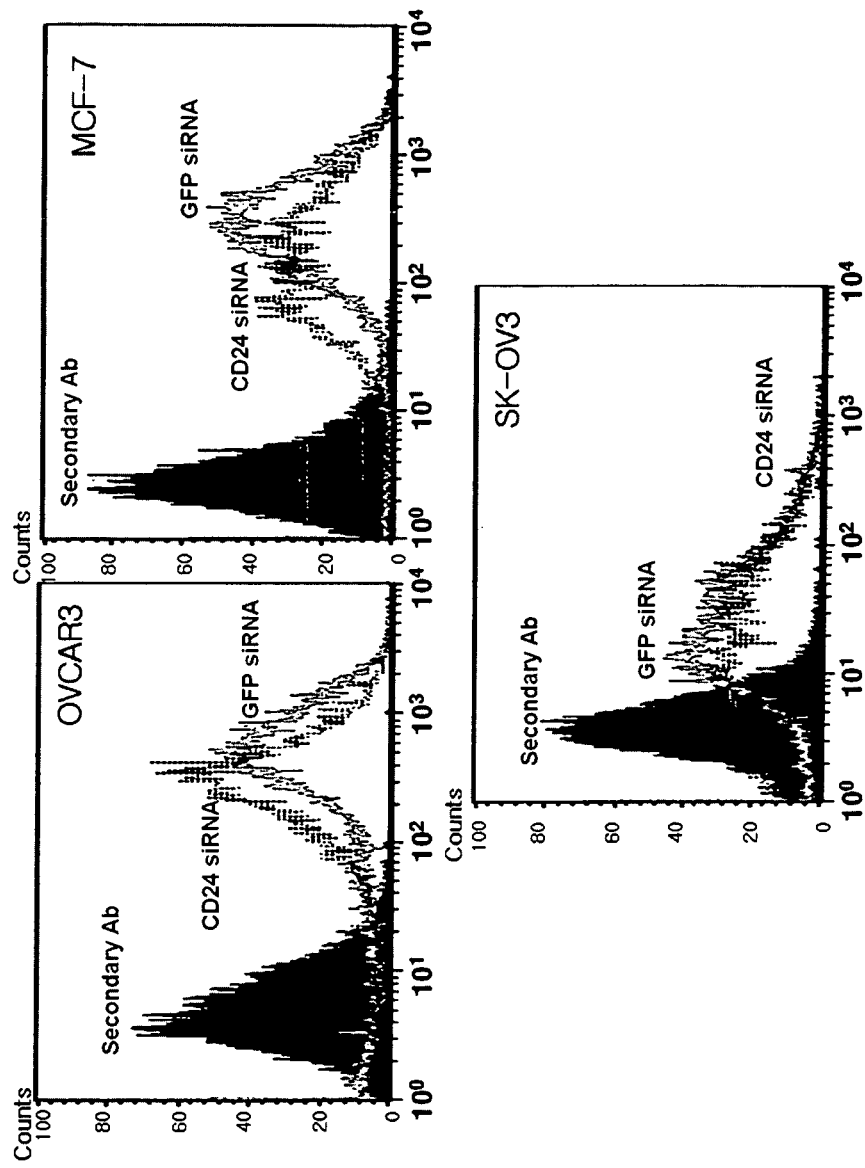

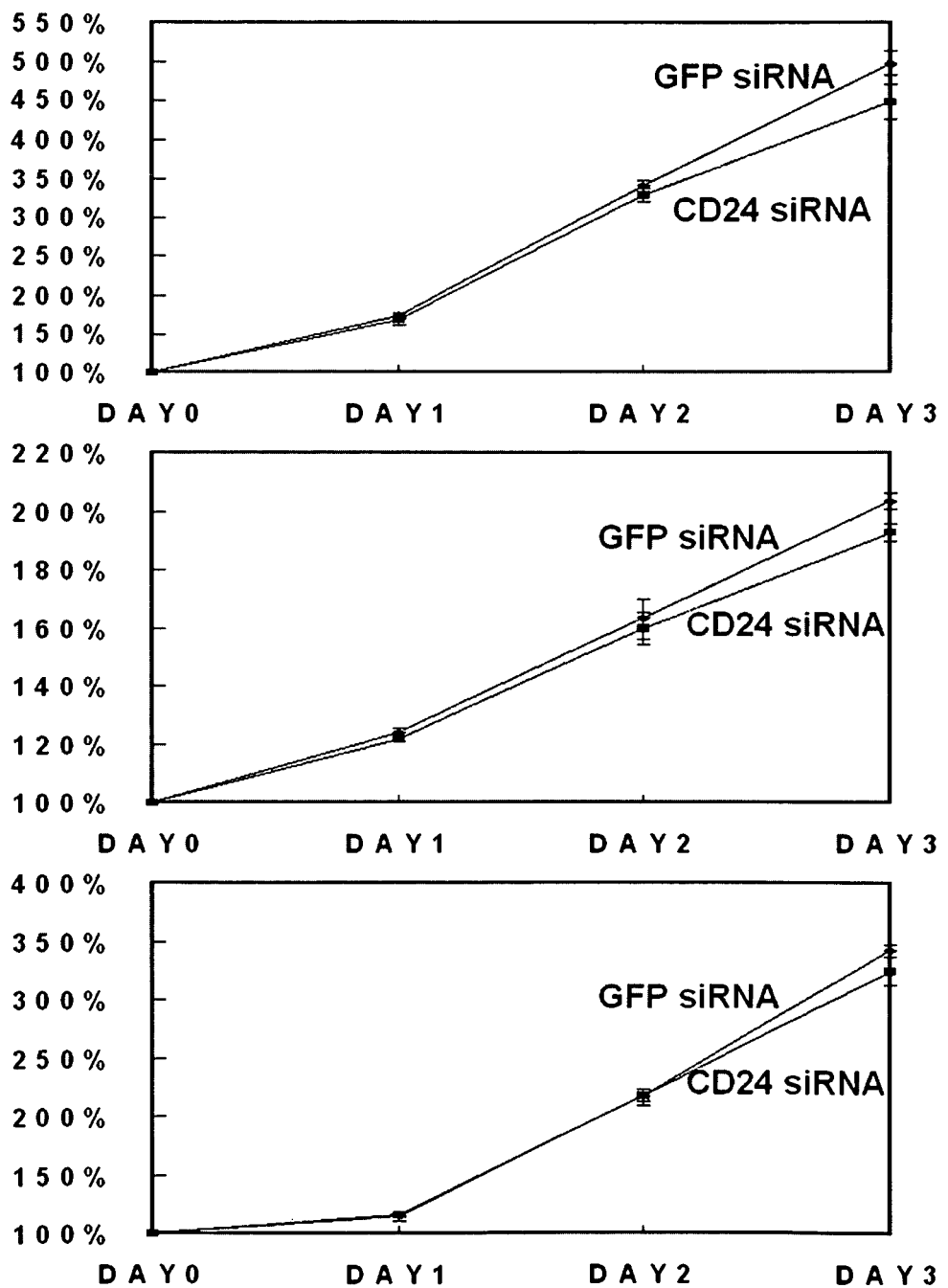
[Fig. 7]

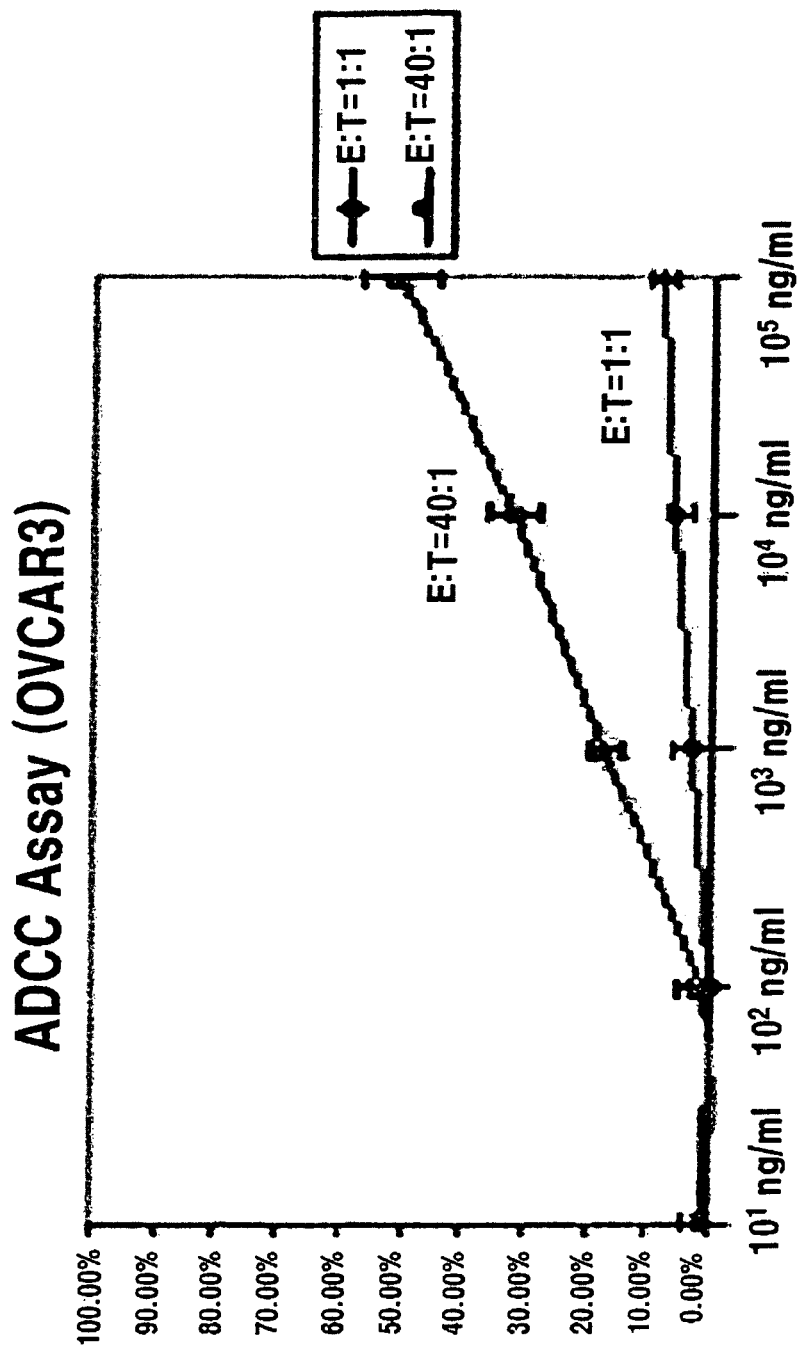
[Fig. 8]

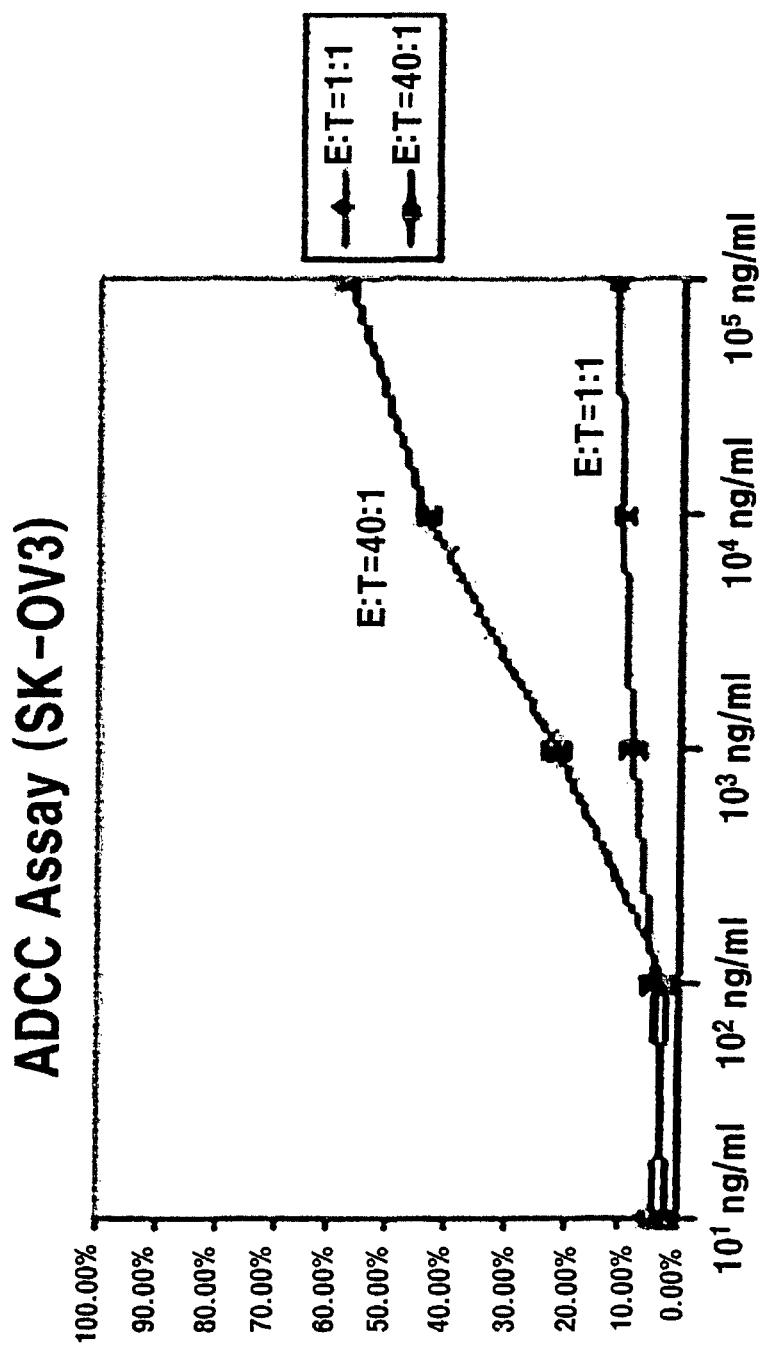
[Fig. 9]

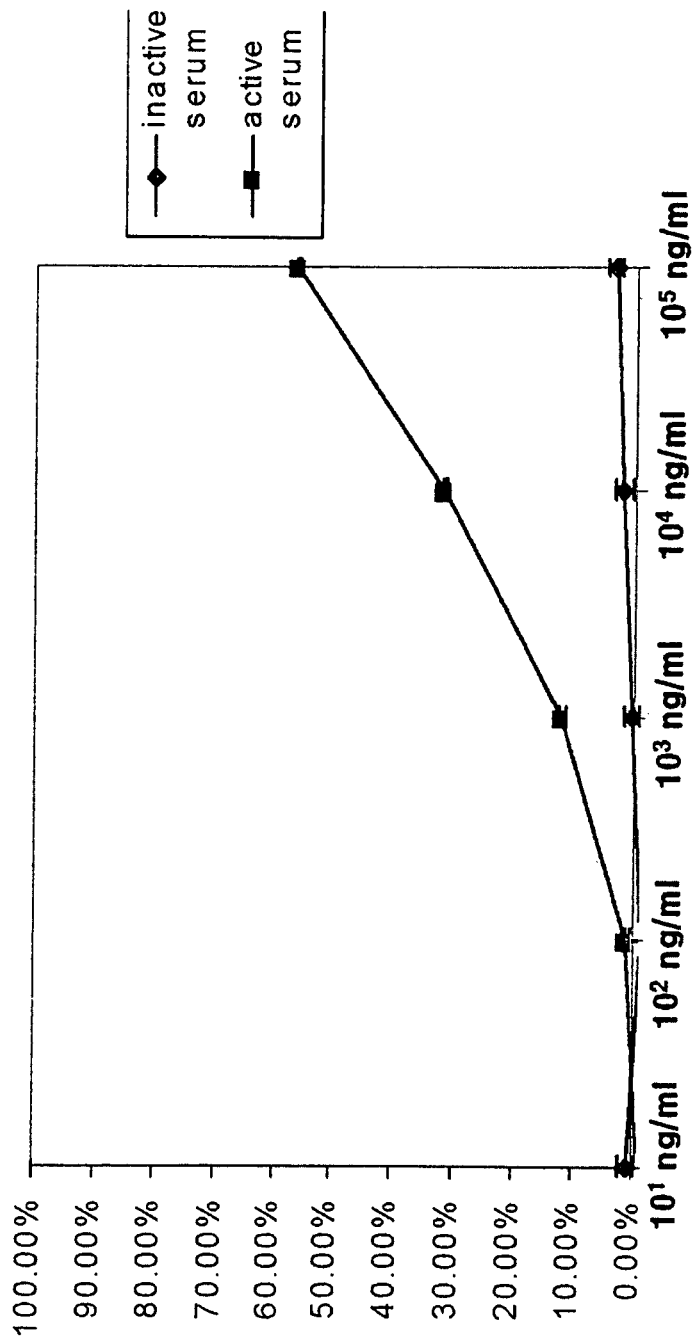
[Fig. 10]

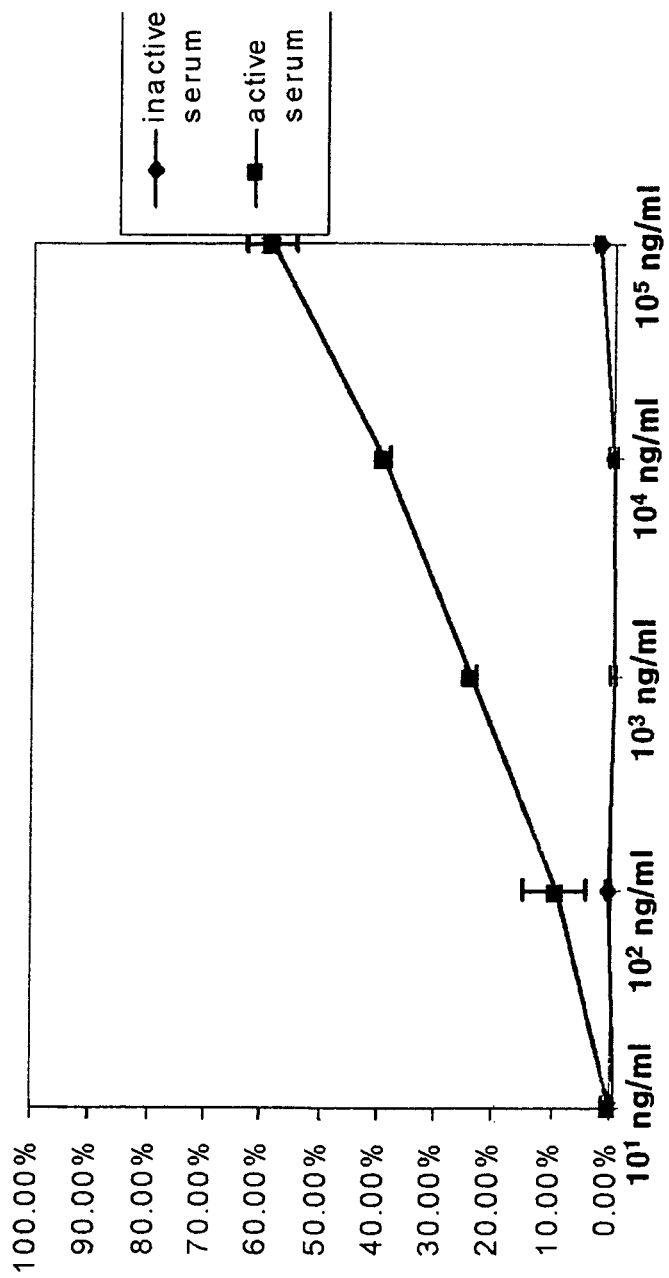

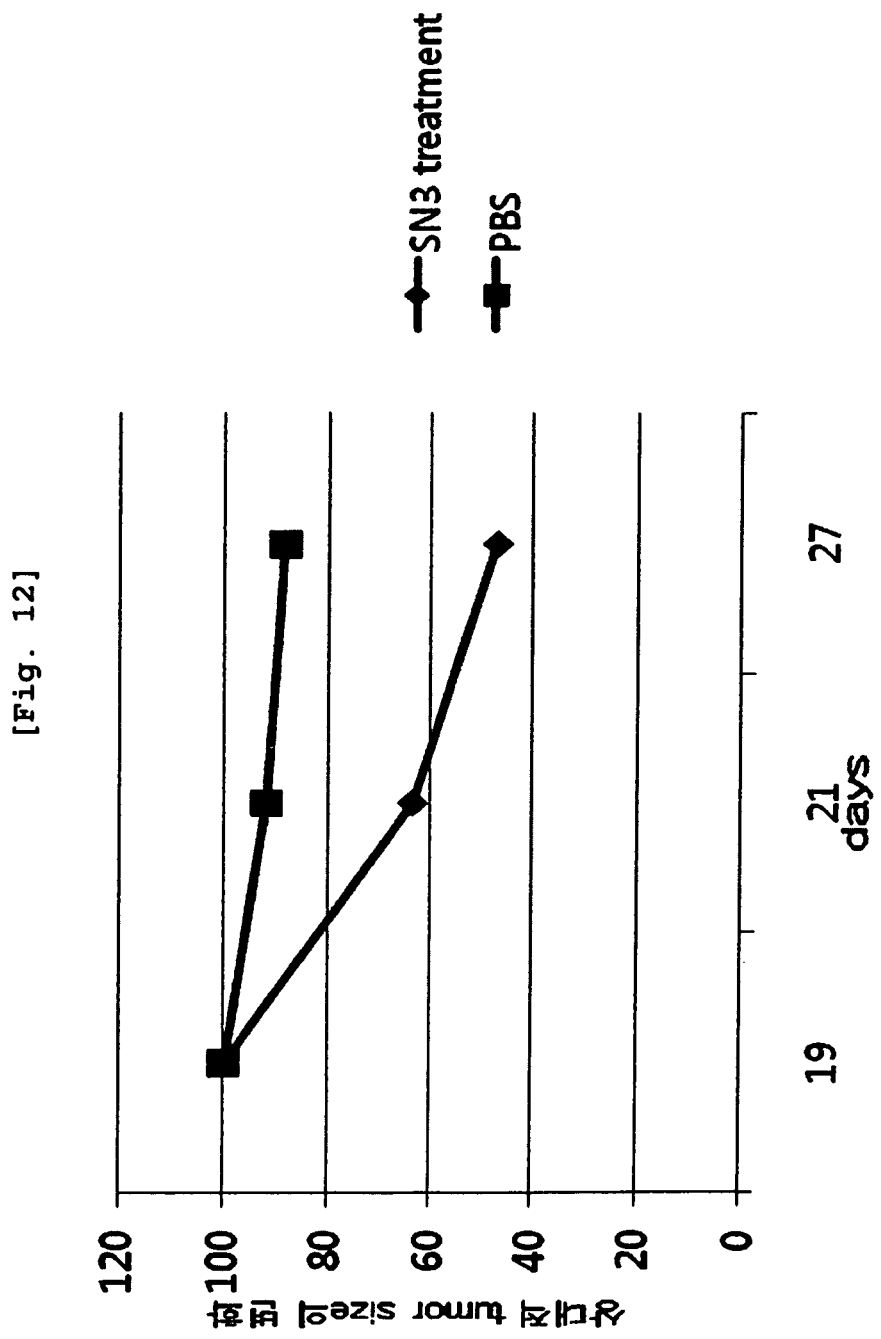
[Fig. 12]

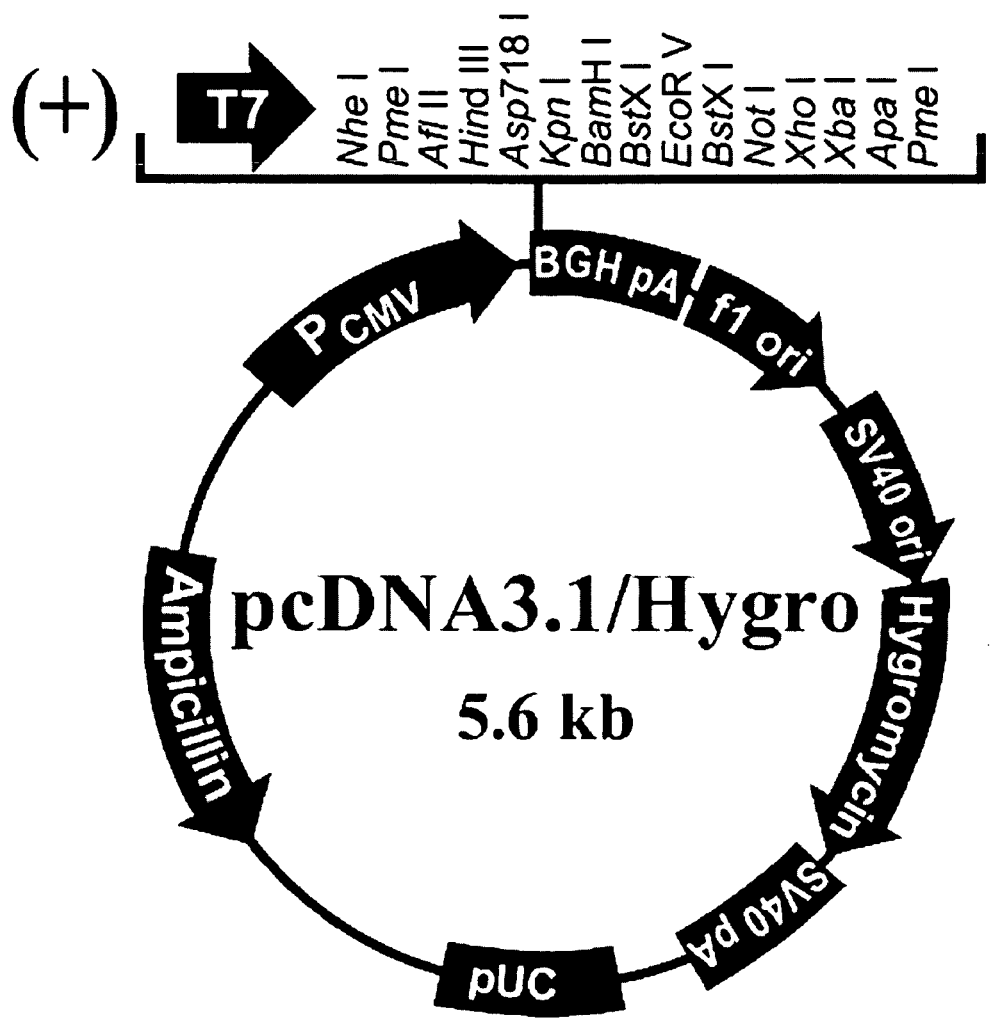
[Fig. 13]

METHOD TO INHIBIT CANCER TARGETING CD24

CROSS REFERENCE TO RELATED APPLICATIONS

This is the U.S. National Stage of PCT Application No. PCT/KR2007/003202, filed Jul. 2, 2007, which was published in English under PCT Article 21(2), which in turn claims the benefit of Korean Application No. 10-2006-0061119, filed Jun. 30, 2006, which is incorporated herein by reference in its entirety.

TECHNICAL FIELD

The present invention relates to a method to inhibit cancer by targeting CD24, more precisely a method to inhibit cancer by targeting CD24 expressed in most cancer cells as an antibody therapeutic agent or by inhibiting the interaction between CD24 and P-selectin.

BACKGROUND ART

To treat cancer, a surgery is generally performed and mostly accompanied with chemo-therapy and radio-therapy. However, these treatment methods have serious side effects of destroying normal tissues and the treatment effect of them varies with patients. To improve the above disadvantage of the conventional methods, a "targeting method" emerges as an alternative, which is to target a specific protein particularly expressed in cancer cells and thus to develop an anticancer agent by using an inhibitor or an antibody that binds to the target protein. This agent cannot bind to or invade into normal tissues but is able to interact specifically with cancer cells, making it a promising agent with reduced side effects.

One example of the "targeting treatment" is immuno therapy, which is a method to kill cancer cells, based on the innate immune system. Particularly, an antibody binding to a cancer specific protein is injected and then bound to the cancer cells to cause immune response, resulting in the death of the cancer cells. Therapeutic antibodies developed so far in USA are approximately 10, which have been used as a therapeutic agent for leukemia or breast cancer. However, a proper immuno-therapy for other cancers has not been developed, yet.

One of the representative method for the immuno-therapy is monoclonal antibody therapy. An antibody has a high selective binding capacity to its target antigen and thus exhibit anticancer effect via natural immune system. One of the constituents of an antibody, Fab domain, forms an antigen binding site and Fc domain responses to those cells involved in immune system to cause immune response. Cancer cells are directly affected by the binding of the Fab domain of an antibody to its target antigen. In the meantime, the bond between Fcγ receptor of an effector cell and Fc domain of an antibody can induce antibody-dependent cell-mediated cytotoxicity and induce cell lysis by mediating Fc-mediated complement reaction (Kabita M D, Madhav V, PNAS, 102: 18; 6243-6244, 2005). Therefore, the monoclonal antibody therapy is in the limelight of the medical field owing to such expecting anti-cancer effect and less side effects.

An antibody is functioning to induce antibody-dependent cell-mediated cytotoxicity (ADCC), complement dependent cytotoxicity (CDC) and phagocytosis at the same time to inhibit cell surface receptors. In general, ADCC and CDC are major mechanisms of immune defense system.

ADCC is a kind of cytotoxicity randomly executed by those cells recognizing Fc receptor such as natural killer cells, leukocytes and macrophages. When a specific antibody is bound to a target protein of a target cell, the target cell becomes lysed by the action of effector cells. The effector cells for ADCC analysis in vitro are peripheral blood mononuclear cells (PBMC) and natural killer cells, and these cells can be obtained from the blood of volunteers.

CDC is induced by the action of a complement in serum, which also causes target cell lysis. The activation of a complement begins with the formation of a complex of C1q, the first element of complement system, and an antibody on a target cell. To analyze CDC, serum without heat-inactivation at 56° C. is used.

In the meantime, CD24 has been identified as a homologous protein of a murine heat-stable antigen (HAS; mouse CD24) in late 1970. HAS is a glycoprotein of a mouse, which is connected to cell membrane by fixed glycosylphosphatidylinositol (GPI) and composed of 31 amino acids in total. Among these amino acids, 16 amino acids are Ser, Thr and Asn residues that can be O-glycosylated and N-glycosylated (Kay R et al, *J immunol* 147:1412-1416, 1991). The potential O-glycosylation sites are mainly located in N-terminal and C-terminal of CD24, so it is expected that CD24 has a dumbbell like shape. Glycosylation of CD24 depends on cell types and the glycosylated molecule has a wide range of molecular weight of 35 kDa-70 kDa (G. Kristiansen et al. J Mol Histology 35:255-262, 2004). Mouse HAS is mostly expressed in hematopoietic cell subpopulation including pro-B lymphocytes but is also found in the brain and epithelial cells of the tissue under the developmental stage (Belvindrah R et al., J Neuroscience 22:3594-3607, 2002).

Human CD24 has a similar expression pattern to mouse HAS but unlike mouse HAS, human CD24 is not expressed in erythrocytes and thymocytes and only found in early stage B-lymphocytes (Kay R et al., *J immunol* 147:1412-1416, 1991). Therefore, CD24 has been used as an early stage B-cell marker. Later, it has been confirmed that CD24 could be used as a marker for epidermal cells of the kidney and the brain under the developmental stage. A CD24 knock-out mouse had no other functional defect but B-lymphocyte development (Nielsen P J et al., *Blood* 89:1245-1258. 1997; Shirasawa T. et al, *Dev Dyn* 198:1-13, 1993), indicating that CD24 is involved in the proliferation and maturation of pro-B-lymphocytes.

According to the recent immunohistochemical studies, CD24 over-expression is observed in various cancer cells. In particular, it was confirmed that once CD24 was found in cytoplasm, metastasis was accelerated. From the immunohistochemical tests, it was confirmed that CD24 over-expression was observed in ovarian cancer (83%), breast cancer (85%), small cell lung cancer (45%), prostatic cancer (48%), pancreatic cancer (72%), rectal cancer (84%), cholangiocarcinoma (51%) and bladder cancer (62%). Comparatively high CD24 expression in lethal cancers showing low survival rate such as ovarian cancer, breast cancer, small cell lung cancer and prostatic cancer suggests that CD24 can be used as a diagnostic marker for those cancers (Krisiansen G. et al., *Am J Pathol,* 161:1215-1221, 2002; Krisiansen G. et al., *Clin cancer Res,* 9:4906-4913, 2003; Krisiansen G. et al., *Br J Cancer,* 88:231-236, 2003; Kristiansen G. et al., *Prostate,* 58:182-192, 2004; Hocob J. et al., *Pancreatology,* 4:454-460, 2004; Samuel E D, *BioMed Central,* 3:3-15, 2004; Min-Cheng S. et al., *Cancer letter,* 1-6, 2005; Yoon-La C. et al. *Archives of Pathology & Laboratory Medicine*, in press). According to the data established by the inventors, CD24 over-expression is also observed in liver cancer, small intestine cancer, large intestine cancer and cervical cancer (LG database).

Therefore, the present inventors performed experiments by treating an antibody against pre-cancer marker CD24 into an ovarian cancer cell line. As a result, cancer was suppressed by CDC and ADCC and so the inventors further completed this invention by confirming that cancer can be inhibited by targeting CD24.

DISCLOSURE

Technical Problem

It is an object of the present invention to provide a therapeutic method for cancer by targeting CD24 expressed in most cancer cells or by inhibiting the interaction between CD24 and P-selectin.

Technical Solution

To achieve the above object, the present invention provides a method to inhibit cancer by using a CD24 specific ligand recognizing specifically CD24 in cancer cells over-expressing CD24.

The present invention also provides a method to inhibit cancer by inhibiting the interaction between CD24 and P-selectin.

The present invention further provides an anticancer agent containing an anti-CD24 antibody as an active ingredient.

The present invention also provides an anticancer agent containing an anti-CD24 antibody as a carrier.

In addition, the present invention provides a method to inhibit cancer comprising the step of co-administration of an anti-CD24 antibody and another anticancer agent.

"Complement dependent cytotoxicity (CDC)" herein indicates the mechanism causing cell death by inducing cell lysis, particularly an antibody bound to a target cell fixes complements to cause membrane attack complex assembly and then a hole is formed in the target cell to cause cell lysis.

"Antibody-dependent cell-mediated cytotoxicity (ADCC)" herein indicates the mechanism in which an IgG antibody binding antigen is more easily killed by natural killer cells.

"Carrier" is a medium used for drug delivery system (DDS), more particularly a medium carrying a drug to a specific target. And "epitope" indicates a specific region of an antigen recognized by an antibody. "Specific recognition" herein means the specific bond between a specific ligand and its receptor.

Hereinafter, the present invention is described in detail.

The present invention provides a method to inhibit cancer by using a CD24 specific ligand specifically recognizing CD24 in cancer cells that over-express CD24.

"Ligand" herein indicates a molecule that is able to form a complex by binding with a specific biomolecule.

The CD24 specific ligand above is preferably an antibody or P-selectin and more preferably an anti-CD24 antibody, but not always limited thereto.

According to the recent studies, CD24 over-expression is observed in various types of cancer cells, in particular when CD24 over-expression was observed in cytoplasm, metastasis was accelerated. For example, CD24 over-expression was observed in ovarian cancer (83%) (Krisiansen G. et al, *Am J Pathol*, 161:1215-1221, 2002), breast cancer (85%) (Krisiansen G. et al, *Clin cancer Res*, 9:4906-4913, 2003), small cell lung cancer (45%) (Krisiansen G. et al, *Br J Cancer*, 88:231-236, 2003), prostatic cancer (48%) (Kristiansen G. et al, *Prostate*, 58:182-192, 2004), pancreatic cancer (72%) (Hocob J. et al, *Pancreatology*, 4:454-460, 2004), rectal cancer (84%) (Samuel E D et al, *BioMed Central*, 3:3-15, 2004), bladder cancer (62%) and cholangiocarcinoma (51%) (Min-Cheng S. et al, *Cancer letter*, 1-6, 2005), and particularly the level of CD24 was comparatively high in lethal cancers such as ovarian cancer, breast cancer, small cell lung cancer, and prostatic cancer, suggesting that CD24 can be used as a diagnostic marker for such cancers showing low survival rate. CD24 over-expression was also observed in liver cancer, small intestine cancer, large intestine cancer and cervical cancer Based on the above foundings, the present inventors investigated whether CD24 specifically expressed in cancer cells could be used as a target for the cancer treatment using an antibody.

Particularly, the inventors performed RT-PCR, Western blotting and FACS and as a result the inventors confirmed over-expression of CD24 in an ovarian cancer cell line (see FIG. 1-FIG. 3). The ovarian cancer cell line, cervical cancer cell line and breast cancer cell line were transfected with siRNA (SEQ. ID. NO: 2). As a result, CD24 expression was reduced (see FIG. 4-FIG. 6) but apoptosis was not significantly changed (see FIG. 7). There was a report saying that CD24 siRNA induced apoptosis (Yuriy Efdorov et al., *RNA*. 2006, 12:1188-96), but this seems to be off-target effect of siRNA.

According to recent reports, the off-target effect, which means non-specific gene expression is reduced by siRNA whether it is a target gene or not, has covered 5-80% of the total test results (Qiu S, et al., *Nucleic Acids Res*. 2005, Mar. 30; 33(6):1834-47). And the off-target effect is expressed mainly as a toxic phenotype. Therefore, the previous CD24 siRNA test result was attributed to the off-target effect and thus CD24 siRNA cannot be used as a cancer treatment agent.

The present invention also provides a method to inhibit cancer by inhibiting the interaction between CD24 and P-selectin.

CD24, an adhesion molecule binding to P-selectin, is considered to be involved in cell-cell interaction (Aigner S. et al., *Blood*, 89:3385-3395, 1997). The only ligand of CD24, P-selectin (CD62P) exists in the activated platelets and the surface of vascular endothelial cells and generally recognizes sialyl Lewis X-epitope expressed massively in human cancer cells. Thus, the sialyl Lewis X-epitope plays a very important role in the interaction between CD24 and P-selectin and further CD24 expression seems to be a key factor in metastasis. CD24-positive cells can interact more easily than CD24-negative cells with P-selectin detected in the activated platelets in blood to form a blood clot. Cancer cells migrate far through blood flow by being carried on the generated blood clot. CD24 can easily adhere to endothelial cells of a target organ to induce metastasis (Aigner S. et al., *FASEB J*, 12:1241-1251. 1997). However, the interaction between CD24 and P-selectin is not observed between lymphocytes and the activated platelets or between lymphocytes and endothelial cells (Aigner S. et al., *Blood* 89:3385-3395, 1997).

An Anti-CD24 monoclonal antibody was once used for clinical tests aiming at the treatment of a disease. Particularly, an anti-CD21 antibody and anti-CD24 antibody produced from a rat were injected into a patient with B-lymphoproliferative disorder. As a result, survival rate was increased and the disease was definitely alleviated (Malika B. et al., *Blood*, 82:3137-3147, 1998).

In the above test, it was noteworthy that serious side effects were not detected among patients treated with the above antibodies. This result suggests that an anti-CD24 antibody might have no significant side effects as a cancer treatment agent. So, CD24 can be used not only as a diagnostic marker but also as a therapeutic agent. However, the target disease in the previous studies were not cancer but B-lymphoproliferative disorder and there is no reports on the applicability of such anti-CD24 antibody as a cancer treatment agent.

CD24 functioning mechanisms and pathological test results have all supported the presumption that CD24 could be an ideal target of the cancer treatment using a monoclonal antibody. Further, the interaction between CD24 and P-selectin can be interrupted by the CD24 antibody and if so, metastasis and invasion into vascular endothelial cells can also be inhibited.

The present inventors investigated whether an anti-CD24 antibody could have anticancer effect. Particularly, Ovarian cancer cells were cultured and recovered, which were marked with Calcein-AM and treated with the CD24 antibody. Complement dependent cytotoxicity (CDC) was induced by adding human serum and then cytotoxicity of the anti-CD24 antibody was measured. As a result, more than 50% of the total cells were killed at the anti-CD24 antibody concentration of $10^5$ ng/ml, indicating that the anti-CD24 antibody had a sufficient cytotoxicity (see FIG. 8 and FIG. 9).

Peripheral blood mononuclear cells (PBMC) were separated from the whole blood of a normal volunteer by using ficol-paque plus (Amersham), which were then marked with Calcein AM and treated with an anti-CD24 antibody. The cells were incubated and lysed to measure the cytotoxicity of the anti-CD24 antibody. As a result, more than 50% of the total cells were killed at the anti-CD24 antibody concentration of $10^5$ ng/ml, which was consistent with the above result, indicating that the anti-CD24 antibody had a sufficient cytotoxicity (see FIG. 10 and FIG. 11).

To investigate the anticancer effect of the anti-CD24 antibody in vivo, the present inventors performed experiments using a xenograft model. To prepare the xenograft model, the CD24 over-expressing cell line SK-OV3 was transfected with a luciferase construct and the resultant cell line was hypodermically injected in the back of a mouse. The luciferase activity was reduced in the mouse treated with the anti-CD24 antibody, compared with the mouse not treated (treated with PBS only) (see FIG. 12). The above result indicates that the anti-CD24 antibody inhibited cancers and therefore had a potential for the use as an anticancer agent.

An anti-CD24 antibody can be purchased or prepared by injecting the CD24 protein (antigen) into an external host according to the conventional method known to those in the art. It is more preferred to prepare the antibody specifically using the amino acid sequence represented by SEQ. ID. NO: 6, the amino acid sequence represented by SEQ. ID. NO: 5, the amino acid sequence of CD24 represented by SEQ. ID. NO: 7, or a part of the sequence or the amino acid sequence and its adjacent sequence along with its glycosylated sequence as an epitope. The external host for the production of the antibody can be a mammal including a mouse, a rat, a sheep and a rabbit. The immunogen can be injected by intramuscular, intra-abdominal or hypodermic injection. And the immunogen can be co-treated with an adjuvant to increase antigenicity. Serum exhibiting titer and specificity to an antigen was collected from blood of an external host and the antibody was separated. Phage display method was hired to produce a humanized antibody which is an antigen specific antibody.

The present invention further provides an anticancer agent containing an anti-CD24 antibody as an active ingredient or a carrier.

The anticancer agent containing the anti-CD24 antibody of the invention as an active ingredient can additionally include one or more effective ingredients having equal or similar functions to the above antibody and might include one or more other anticancer agents.

The other anticancer agents herein include a chemotherapeutic agent, a radiotherapeutic agent or an immunotherapeutic agent. The chemotherapeutic agent is exemplified by ifosfamide, doxorubicin HCL, bleomycin, mitomycin, etoposide, vinblastine, vincristine, vinorelbin, paclitaxel, docetaxel, irinotecan, topotecan, hydroxyurea, cyclophosphamide, melphalan, chlorambucil, carmustine, cisplatin, carboplatin, fluorouracil, capecitabine, gemcitabine, imatinib and goserelin acetate, but not always limited thereto.

The radiotherapeutic agent herein includes every nuclide emitting radioactive rays usable for the cancer treatment including x-ray, gamma-ray, electron beam, photon, alpha-particle and neutron, etc. And the above nuclide is exemplified by I-131, Co-60, Co-57, Ir-192, Ho-166, P-32, V-48, Au-198, Tc-99m, I-125, Dy-165, Re-188, Er-169, Sm-153, Y-90, Pd-109 and Sr-89, but not always limited thereto. Such radioactive rays are preferably treated as being carried in a carrier such as chitosan not to leak out of the lesion and to be accumulated on the local lesion only.

The immunotherapeutic agent herein can be a cytokine Or an antigen specific antibody. The cytokine is exemplified by interleukin-1 (IL-1), IL-2, IL-4, IL-5, IL-6, IL-7, IL-10, IL-12, IL-15, IL-18, CSF-GM, CSF-G, IFN-γ, IFN-α, TNF, TGF-β, FLT-3 ligand and CD40 ligand, but not always limited thereto. The antigen specific antibody is exemplified by Rituxan, Herceptin, Zevalin, Erbitux, Mylotarg, Campath-1H, Zenapax, Remicade and Enbrel, and preferably selected according to the types and kinds of cancers and antigens expressed therein.

The anticancer agent of the present invention can also include, in addition to the above-mentioned effective ingredients, one or more pharmaceutically acceptable carriers for the administration. The pharmaceutically acceptable carrier can be selected or be prepared by mixing more than one ingredients selected from the group consisting of saline, sterilized water, Ringer's solution, buffered saline, dextrose solution, maltodextrose solution, glycerol and ethanol. Other general additives such as anti-oxidative agent, buffer solution, bacteriostatic agent, etc, can be added. In order to prepare injectable solutions, pills, capsules, granules or tablets, diluents, dispersing agents, surfactants, binders and lubricants can be additionally added. The anticancer agent of the present invention can further be prepared in suitable forms for each disease or according to ingredients by following the method represented in Remington's Pharmaceutical Science (the newest edition), Mack Publishing Company, Easton Pa.

The anticancer agent containing an anti-CD24 antibody as an active ingredient of the present invention can be administered orally or parenterally. The parenteral administration is exemplified by hypodermic injection, intravenous injection, intramuscular injection and intrathoracic injection. To prepare formulations for parenteral administration, solutions or suspensions are prepared by mixing the compound of formula 1 or 2 with a stabilizer or a buffer in water. The prepared solutions or suspensions are formulated by the unit dosage of an ampoule or a vial.

The effective dosage of the anticancer agent of the invention can be determined according to weight, age, gender, health condition, diet, administration frequency, administration method, excretion and severity of a disease. The anticancer agent of the invention includes the anti-CD24 antibody by the concentration of 0.1 μg/ml~500 μg/ml, and preferably 1

μg/ml~50 μg/ml. Administration frequency is once a month or preferably a few times a month.

When the anti-CD24 antibody is used as a carrier for the anticancer agent of the invention, the conventional anticancer materials, drugs or toxic materials can be loaded in the antibody before formulation (Korean Patent Publication Nos. 1990-0007408 "antibody-drug conjugate"; 1990-0002804, "cytotoxic drug conjugate and preparation method thereof"; 1990-0002803 "cytotoxic drug conjugate", Eli Lilly and Company).

The present invention also provides a method to inhibit cancer comprising the step of co-administration of an anti-CD24 antibody and another anticancer agent.

The another anticancer agent herein includes the above-mentioned chemotherapeutic agent, radiotherapeutic agent or immunotherapeutic agent. Co-treatment of the anticancer agent of the invention containing the anti-CD24 antibody with a conventional anticancer agent will be more effective to inhibit cancer.

DESCRIPTION OF DRAWINGS

The application of the preferred embodiments of the present invention is best understood with reference to the accompanying drawings, wherein:

FIG. 1 is a diagram illustrating the CD24 expression in OVCAR3 and SK-OV3 confirmed by FACS using anti-CD24-IgG-FITC.

FIG. 2 is a diagram illustrating the CD24 expression in OVCAR3 and SK-OV3 confirmed by Western blotting.

FIG. 3 is a diagram illustrating that SK-OV3 was loaded on a cover glass coated with PLL (polly-L-Lysin), to which an anti-CD24 mouse antibody and a goat-anti-mouse IgG-FITC antibody were added, followed by observation of CD24 level in the cells under a confocal microscope.

FIG. 4 is a diagram illustrating that the CD24 expression was reduced specifically by CD24 specific siRNA confirmed by RT-PCR.

FIG. 5 is a diagram illustrating that the CD24 expression was reduced after the treatment of CD24 specific siRNA confirmed by Western blotting using an anti-CD24 mouse antibody.

FIG. 6 is a diagram illustrating that the CD24 expression was reduced by the treatment of CD24 specific siRNA confirmed by FACS using anti-CD24-IgG-FITC.

FIG. 7 is a graph illustrating the numbers of cells observed for three days after the treatment of CD24 specific siRNA.

FIG. 8 is a diagram illustrating the cytotoxicity in OVCAR3, particularly OVCAR3 was stained with calcein AM and an anti-CD24 mouse antibody was treated thereto at different concentrations, then PBMC was added, followed by measuring the cytotoxicity at 485/535 nm.

FIG. 9 is a diagram illustrating the cytotoxicity in SK-OV3 measured by the same manner as described in FIG. 8.

FIG. 10 is a diagram illustrating the cytotoxicity in OVCAR3 measured at 485/535 nm. Particularly, OVCAR3 was stained with calcein AM, to which an anti-CD24 mouse antibody was treated at different concentrations. Activated human serum and inactivated human serum were added thereto respectively and then the cytotoxicity was measured at 485/535 nm.

FIG. 11 is a diagram illustrating the cytotoxicity in SK-OV3 measured by the same manner as described in FIG. 10.

FIG. 12 is a graph illustrating the anticancer effect of the anti-CD24 antibody (SN3) in a xenograft model.

FIG. 13 is a schematic diagram of the vector pcDNA3.1/Hygro(+) (Invitrogen, USA) used for the construction of a luciferase expression vector.

MODE FOR INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Cell Line and Antibody

OVCAR3 and SK-OV3 (KOREAN CELL LINE BANK, KCLB), ovarian cancer cell lines, and MCF-7, a breast cancer cell line, were cultured in RPMI1640 (Sigma Chemical Co.) supplemented with 10% FBS and antibiotics in a 37° C., 5% $CO_2$ incubator with 100% humidity. CHO-DG44 (Chinese Hamster Ovary cell, PanGen Biotech, Korea) was cultured in MEM (GIBCO) supplemented with 10% certificated fetal bovine serum (GIBCO) and antibiotics. The mouse monoclonal antibody CD24 was purchased from Neomarker (Labvision, clone SN3).

Example 2

CD24 Specific siRNA

OVCAR3 and SK-OV3, ovarian cancer cell lines, and MCF-7, a breast cancer cell line, were transformed with CD24 specific siRNA. The CD24 specific siRNA was obtained from Dharmacon via siRNA design center of Dharmacon home page (www.dharmacon.com). The target sequence of the CD24 siRNA was 5'-CCAAATCCAAC-TAATGCCA-3' (SEQ. ID. NO: 1) and transformation with siRNA (Oligofectamin2000, Invitrogen) was performed according to Dharmacon's siRNA treatment protocol. 72 hours after the siRNA treatment, cell number was measured. And CD24 level was measured by RT-PCR, Western blotting and FACS. As a result, CD24 level was lowered by the siRNA treatment but apoptosis was not significantly changed.

Example 3

Western Blotting

Immuno-blotting was performed to detect CD24 expression in cells. The cells were lysed using RIPA lysis buffer (150 mM NaCl, 10 mM Tris-HCl(pH 7.4) 5 mM EDTA, 0.1% SDS, 0.5% deoxycholate and 1% NP-40), followed by western blotting. The anti-CD24 mouse antibody was purchased from Lab Vision and diluted at the ratio of 1:2000. From the result of Western blotting, it was confirmed that the CD24 over-expression was observed in both OVCAR3 and SK-OV3 and the CD24 expression was reduced by the treatment of CD24 specific siRNA, suggesting that the detected band was CD24. Considering the darkness of the band, CD24 level in OVCAR3 was higher than that in SK-OV3.

Example 4

RT-PCR

Human CD24 cDNA was obtained by amplifying CD24 RNA of OVCAR3 using Superscript II RNaseH reverse transcriptase (Solgent) and Taq polymerase (Solgent). The primer sequences used for the amplification were 5'-AACGTCT-TCTAAATTTCCCC-3' (forward, SEQ. ID. NO: 3) and 5'-TGGCATTCATCATCTAGTCA-3' (reverse, SEQ. ID. NO: 4). PCR was performed as follows; predenaturation at 95° C. for 5 minutes, denaturation at 94° C. for 30 seconds, annealing at 55° C. for 30 seconds, polymerization at 72° C. for 1 and half minute, 20 cycles from denaturation to polymerization, and final extension at 72° C. for 10 minutes. From the result of RT-PCR, it was confirmed that CD24 was overexpressed in OVCAR3 and SK-OV3, and the expression was decreased by the treatment of CD24 specific siRNA and thus the detected band was considered as CD24 band.

Example 5

FACS

The cells were treated with trypsin and recovered. The recovered cells were resuspended in FACS buffer (PBS/0.1% sodium azide/0.5% BSA) at the concentration of $10^6$ cells/ml. FITC-labeled anti-CD24 murin IgG antibody (BioLegend) was added thereto at the concentration of 20 μl per $10^5$ cells, which was incubated in iced water for 30 minutes. After the incubation, 3 ml of FACS buffer was added, followed by centrifugation at 1000 rpm for 10 minutes. Supernatant was eliminated and the cells were resuspended in 0.5 ml PBS. FACS was performed using DB FACS Machine. As a result, the CD24 over-expression was observed in both OVCAR3 and SK-OV3 and the expression was reduced by the treatment of CD24 specific siRNA, suggesting that the detected peak was CD24. From the comparison of RI values, it was confirmed that CD24 level was higher in OVCAR3 than in SK-OV3, which was consistent with the result of Western blotting.

Example 6

Complement Dependent Cytotoxicity

Complement dependent cytotoxicity (CDC) was measured by Calcein-AM release assay which has similar sensitivity to $Cr^{51}$ assay generally used.

The cultured SK-OV3 and OVCAR3 were treated with trypsin and then recovered. The cells were washed with RPMI/10% FBS, followed by incubation in RPMI supplemented with 3 ml of 5 μM Calcein AM (Sigma) at 37° C. for 30 minutes to label with Calcein-AM. The labeled cells were washed twice with PBS and resuspended in RPMI 10% FBS. The cells were placed in a 96-well flat-bottom microplate at the concentration of $5\times10^3$ cells (40 μl)/well, to which 20 μl of anti-CD24 antibody solution (0-$10^5$ ng/ml) (CD24 antibody was diluted in RPMI1640 at different concentrations) was added, followed by incubation for 30 minutes.

40 μl of RPMI supplemented with 25% human serum was added to the above plate to induce CDC reaction, followed by filtering with a 0.22 μm filter to make the final concentration of human serum as 10%. To prepare a negative control, 25% human serum was inactivated at 56° C. for one hour and filtered. After 4 hours of incubation at the above concentrations respectively, the cells were centrifuged at 2000 rpm for 10 minutes. 50 μl of the supernatant was placed in a Black Nunclon Surface plate (Nunc). Arbitrary fluorescent unit (AFU) was measured using Flexstation II (Molecular Devices) at 485/535 nm. % specific cell lysis was calculated by the following formula: [(AFU experimental release−AFU spontaneous release)/(AFU maximal release−AFU spontaneous release)]×100. AFU spontaneous release was defined as Calcein AM release in the absence of an antibody and AFU maximal release was measured after target cell lysis using RPMI supplemented with 2% Triton X-100. As a result, cell lysis was significant in the presence of an antibody, compared with cell lysis in the absence of an antibody, and cell death was increased the anti-CD24 antibody concentration dependently. And, more than 50% of the total cells were killed at the anti-CD24 antibody concentration of $10^5$ ng/ml.

Example 7

Antibody-Dependent Cell-Mediated Cytotoxicity

Peripheral blood mononuclear cells (PBMC), the immuno effector cells, were separated from the whole blood of a normal donor by using ficol-paque plus (Amersham). The separated cells were resuspended in RPMI/10% FBS. SK-OV3 and OVCAR3 were stained with 5 μM Calcein AM at 37° C. for 30 minutes by the same manner as described in the above example and then washed twice.

SK-OV3 and OVCAR3 in RPMI/10% FBS ($5\times10^3$ cells/40 ul) were placed in a 96-well flat-bottom microplate, to which 20 μl of anti-CD24 antibody solution (0-$10^5$ ng/ml) was added, followed by incubation for 30 minutes. The effector cells, PBMC, were added (the ratio of E:T=20:1 and 50:1), followed by further incubation for 4 hours. Then, centrifugation was performed at 2000 rpm for 10 minutes and the supernatant was placed in a Black Nunclon Surface plate (Nunc). Arbitrary fluorescent unit (AFU) was measured using Flexstation II (Molecular Devices) at 485/535 nm. % specific cell lysis was calculated by the following formula: [(AFU experimental release−AFU spontaneous release)/(AFU maximal release−AFU spontaneous release)]×100. AFU spontaneous release was defined as Calcein AM release in the absence of an antibody and AFU maximal release was measured after target cell lysis using RPMI supplemented with 2% Triton X-100. The result was consistent with that of CDC assay, which is cell lysis was more significant in the presence of an antibody than in the absence of an antibody and cell death depended on the concentration of the anti-CD24 antibody. Cytotoxicity was increased with the increase of PBMC. And more than 50% of the total cells were killed when the anti-CD24 antibody concentration was $10^5$ ng/ml and the ratio of cells each expressing PBMC and CD24 was 40:1.

Example 8

Anticancer Effect of the Anti-CD24 Antibody in a Xenograft Model

The in vivo anticancer effect of the anti-CD24 antibody of the present invention was measured in a xenograft model.
<8-1> Construction of a Luciferase Expression Vector A luciferase expression vector was constructed using pcDNA3.1/Hygro(+) (Invitrogen, USA, FIG. 13) and pRevTRE/luc (Clontech, USA).

pRevTRE/luc vector is not the kind of vector used for preparing a stable cell line. Thus, only luciferase encoding region of the vector was amplified by PCR. The primer set used for PCR was as follows:

```
Sense primer:
                                      SEQ. ID. NO: 8
acttaagcttgccaccatggaagacgccaaaaacataa;
and Antisense primer:
                                      SEQ. ID. NO: 9
tagtggatccttacacggcgatctttccgc;.
```

The PCR product was digested with Hind III and BamHI, which was then inserted into Hind III and Bam HI sites of pcDNA3.1/Hygro(+) to construct a luciferase expression vector. *E. coli* (DH5α) was transfected with the vector to amplify the DNA.

<8-2> Establishment of a Xenograft Model

SK-OV3, a CD24 over-expressing cell line, was transfected with the luciferase expression vector prepared in example <8-1> to establish a stable cell line. The obtained SK-OV3 luciferase cell line ($5\times10^6$) was resuspended in PBS (100 ul). Female Balb-C nude mice (central Lab. Animal Inc., Korea) at 5 weeks were raised for 30 days in College of Pharmacy, Kangwon National University, Korea. The prepared cell solution was injected hypodermically under the back of the mouse to establish a xenograft model.

<8-3> Measurement of Cancer Size

The xenograft model prepared in example <8-2> was raised for 19 days. When cancer formation was confirmed, 160 ul of anti-CD24 antibody (1 mg/ml, SN3, Neomark, USA) was injected in the tail vein. For a control, only PBS was injected instead of anti-CD24 antibody in the tail vein. One week later, SN3 (80 ul) and PBS (80 ul) were respectively injected in the tail vein once a week.

The mice were anesthetized with isofluran. To measure the luciferase activity, luciferin was injected in the abdominal cavity of the mouse. 15 minutes later, bioluminescence signal released by luciferase was measured by using IVIS200 (Xenogen, USA).

As a result, the cancer size was reduced (approximately 40%) in the mouse treated with the anti-CD24 antibody, compared with that in the mouse not-treated with the anti-CD24 antibody.

INDUSTRIAL APPLICABILITY

As explained hereinbefore, CD24 is mostly over-expressed in cancer cells, and the higher the CD24 expression, the faster the metastasis is. Thus, the present invention provides a method to inhibit cancer or metastasis by targeting CD24, which is expected to contribute greatly to the treatment of various cancers.

SEQUENCE LIST TEXT

SEQ. ID. NO: 1 is the target sequence of CD24 siRNA (5'-CCAAATCCAACTAATGCCA-3').

SEQ. ID. NO: 2 is the sequence of CD24 siRNA (5'-ccaaauccaa cuaaugcca-3').

SEQ. ID. NO: 3 is the sequence of a forward primer for the amplification of CD24 (5'-AACGTCTTCTAAATTTCCCC-3').

SEQ. ID. NO: 4 is the sequence of a reverse primer for the amplification of CD24 (5'-TGGCATTCATCATCTAGTCA-3').

SEQ. ID. NO: 5 is the epitope sequence of a CD24 antibody (Leu Ala Pro).

SEQ. ID. NO: 6 is the epitope sequence of a CD24 antibody (Ser Glu Thr Thr Thr Gly Thr Ser Ser).

SEQ. ID. NO: 7 is the whole peptide sequence of CD24 (Met Gly Arg Ala Met Val Ala Arg Leu Gly Leu Gly Leu Leu Leu Leu Ala Leu Leu Leu Pro Thr Gln Ile Tyr Ser Ser Glu Thr Thr Thr Gly Thr Ser Ser Asn Ser Ser Gln Ser Thr Ser Asn Ser Gly Leu Ala Pro Asn Pro Thr Asn Ala Thr Thr Lys Ala Ala Gly Gly Gly Ala Leu Gln Ser Thr Ala Ser Leu Phe Val Val Ser Leu Ser Leu Leu His Leu Tyr Ser).

SEQ. ID. NO: 8 is the sequence of a forward primer for the amplification of a luciferase encoding region of pRevTRE/luc vector (5'-acttaagcttgccaccatggaagacgccaaaaacataa-3').

SEQ. ID. NO: 9 is the sequence of a reverse primer for the amplification of a luciferase encoding region of the pRevTRE/luc vector (5'-tagtggatccttacacggcgatctttccgc-3').

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

---

The invention claimed is:

1. A method of inhibiting cancer overexpressing CD24, comprising:
   administering a therapeutically effective amount of an anti-CD24 antibody to a subject having cancer.

2. The method according to claim 1, wherein the antibody specifically recognizes the amino acid sequence of CD24 represented by SEQ. ID. NO: 7.

3. The method according to claim 1, wherein the antibody has complement dependent cytotoxicity and antibody-dependent cell-mediated cytotoxicity.

4. The method according to claim 1, wherein the cancer overexpressing CD24 is ovarian cancer, breast cancer, small cell lung cancer, prostatic cancer, pancreatic cancer, rectal cancer, bladder cancer, liver cancer, small intestine cancer, large intestine cancer, cervical cancer or cholangiocarcinoma.

5. A method of inhibiting cancer overexpressing CD24, comprising:
   co-administering a therapeutically effective amount of an anti-CD24 antibody and another anticancer agent to a subject having cancer.

6. The method according to claim 5, wherein another anticancer agent is a chemotherapeutic agent, a radiotherapeutic agent or an immunotherapeutic agent.

7. The method according to claim 6, wherein the chemotherapeutic agent is one or more compounds selected from the group consisting of ifosfamide, doxorubicin HCL, bleomycin, mitomycin, etoposide, vinblastine, vincristine, vinorelbin, paclitaxel, docetaxel, irinotecan, topotecan, hydroxyurea, cyclophosphamide, melphalan, chlorambucil, carmustine, cisplatin, carboplatin, fluorouracil, capecitabine, gemcitabine, imatinib and goserelin acetate.

8. The method according to claim 6, wherein the radiotherapeutic agent is a nuclide emitting one or more radioactive rays selected from the group consisting of x-ray, gamma-ray, electron beam, photon, alpha-particle and neutron.

9. The method according to claim 8, wherein the nuclide is selected from the group consisting I-131, Co-60, Co-57, Ir-192, Ho-166, P-32, V-48, Au-198, Tc-99m, I-125, Dy-165, Re-188, Er-169, Sm-153, Y-90, Pd-109 and Sr-89.

10. The method according to claim 6, wherein the immunotherapeutic agent is a cytokine or an antigen specific therapeutic antibody.

11. The method according to claim 10, wherein the cytokine is one or more compounds selected from the group consisting of interleukin-1 (IL-1), IL-2, IL-4, IL-5, IL-6, IL-7, IL-10, IL-12, IL-15, IL-18, CSF-GM, CSF-G, IFN-γ, IFN-α, TNF, TGF-β, FLT-3 ligand and CD40 ligand.

12. The method according to claim 10, wherein the antigen specific therapeutic antibody is selected from the group consisting of Rituxan, Herceptin, Zevalin, Erbitux, Mylotarg, Campath-1H, Zenapax, Remicade and Enbrel.

13. The method according to claim 5, wherein the anti-CD24 antibody has complement dependent cytotoxicity and antibody-dependent cell-mediated cytotoxicity.

14. The method according to claim 5, wherein the cancer overexpressing CD24 is ovarian cancer, breast cancer, small cell lung cancer, prostatic cancer, pancreatic cancer, rectal cancer, bladder cancer, liver cancer, small intestine cancer, large intestine cancer, cervical cancer or cholangiocarcinoma.

15. The method according to claim 5, wherein the anti-CD24 antibody specifically recognizes the amino acid sequence of CD24 represented by SEQ. ID. NO: 7.

* * * * *

SEQUENCE LISTING

```
<160> NUMBER OF SEQ ID NOS: 9

<210> SEQ ID NO 1
<211> LENGTH: 19
<212> TYPE: DNA
<213> ORGANISM: Artificial Sequence
<220> FEATURE:
<223> OTHER INFORMATION: CD24 targeting sequence

<400> SEQUENCE: 1
ccaaatccaa ctaatgcca                                                   19

<210> SEQ ID NO 2
<211> LENGTH: 19
<212> TYPE: RNA
<213> ORGANISM: Artificial Sequence
<220> FEATURE:
<223> OTHER INFORMATION: siRNA sequence to CD24

<400> SEQUENCE: 2
ccaaauccaa cuaaugcca                                                   19
```

-continued

```
<210> SEQ ID NO 3
<211> LENGTH: 20
<212> TYPE: DNA
<213> ORGANISM: Artificial Sequence
<220> FEATURE:
<223> OTHER INFORMATION: primer for CD24

<400> SEQUENCE: 3
aacgtcttct aaatttcccc                                                   20

<210> SEQ ID NO 4
<211> LENGTH: 20
<212> TYPE: DNA
<213> ORGANISM: Artificial Sequence
<220> FEATURE:
<223> OTHER INFORMATION: primer for CD24

<400> SEQUENCE: 4
tggcattcat catctagtca                                                   20

<210> SEQ ID NO 5
<211> LENGTH: 3
<212> TYPE: PRT
<213> ORGANISM: Artificial Sequence
<220> FEATURE:
<223> OTHER INFORMATION: epitope of anti-CD24 antibody

<400> SEQUENCE: 5

Leu Ala Pro
1

<210> SEQ ID NO 6
<211> LENGTH: 9
<212> TYPE: PRT
<213> ORGANISM: Artificial Sequence
<220> FEATURE:
<223> OTHER INFORMATION: epitope of anti-CD24 antibody

<400> SEQUENCE: 6

Ser Glu Thr Thr Thr Gly Thr Ser Ser
1               5

<210> SEQ ID NO 7
<211> LENGTH: 81
<212> TYPE: PRT
<213> ORGANISM: Homo sapiens
<220> FEATURE:
<221> NAME/KEY: PEPTIDE
<222> LOCATION: (1)..(81)
<223> OTHER INFORMATION: CD24 whole peptide sequence

<400> SEQUENCE: 7

Met Gly Arg Ala Met Val Ala Arg Leu Gly Leu Gly Leu Leu Leu Leu
1               5                   10                  15

Ala Leu Leu Leu Pro Thr Gln Ile Tyr Ser Ser Glu Thr Thr Thr Gly
            20                  25                  30

Thr Ser Ser Asn Ser Ser Gln Ser Thr Ser Asn Ser Gly Leu Ala Pro
        35                  40                  45

Asn Pro Thr Asn Ala Thr Thr Lys Ala Ala Gly Gly Ala Leu Gln
        50                  55                  60

Ser Thr Ala Ser Leu Phe Val Val Ser Leu Leu His Leu Tyr
65                  70                  75                  80

Ser
```

-continued

```
<210> SEQ ID NO 8
<211> LENGTH: 38
<212> TYPE: DNA
<213> ORGANISM: Artificial Sequence
<220> FEATURE:
<223> OTHER INFORMATION: primer 1

<400> SEQUENCE: 8
acttaagctt gccaccatgg aagacgccaa aaacataa                              38

<210> SEQ ID NO 9
<211> LENGTH: 30
<212> TYPE: DNA
<213> ORGANISM: Artificial Sequence
<220> FEATURE:
<223> OTHER INFORMATION: primer 2

<400> SEQUENCE: 9
tagtggatcc ttacacggcg atctttccgc                                       30
```